United States Patent [19]
Furuyama et al.

[11] Patent Number: 5,726,622
[45] Date of Patent: Mar. 10, 1998

[54] DEW SENSOR HAVING A CONDUCTIVE POWER-CONTAINING MOISTURE SENSING MATERIAL DISPOSED BETWEEN OPPOSING ELECTRODES

[75] Inventors: Shizuo Furuyama; Nobuharu Tsukiji, both of Osaka, Japan

[73] Assignee: Matsushita Electric Industrial Co., Ltd., Kadoma, Japan

[21] Appl. No.: 668,164

[22] Filed: Jun. 21, 1996

[30] Foreign Application Priority Data

Jun. 21, 1995 [JP] Japan ................. 7-154324

[51] Int. Cl.$^6$ ................................. H01C 7/00
[52] U.S. Cl. ........................................ 338/35
[58] Field of Search .................. 338/34, 35, 308, 338/309; 73/335.05, 335.06

[56] References Cited

U.S. PATENT DOCUMENTS

| | | | |
|---|---|---|---|
| 4,263,576 | 4/1981 | Murata et al. | 338/35 |
| 4,386,336 | 5/1983 | Kinomoto et al. | 338/35 |
| 4,433,320 | 2/1984 | Murata et al. | 338/35 |
| 4,450,429 | 5/1984 | Murata | 338/35 |
| 5,393,404 | 2/1995 | Greenblatt et al. | 204/430 |

*Primary Examiner*—Edward Tso
*Attorney, Agent, or Firm*—Wenderoth, Lind & Ponack

[57] ABSTRACT

A dew sensor used in a video tape recorder, and the like, can be mounted on a printed circuit board remote from the cylinder. A pair of electrodes are formed on an insulated substrate, a moisture sensing material is disposed on the insulated substrate containing the pair of electrodes, and conductive powder is dispersed therein. The moisture sensing material is produced by reaction of a moisture absorbing resin having a hydrophilic group and an epoxy group, and a hardener containing a hydrazine derivative having a hydantoin skeleton, and, optionally, a long chain diamine compound.

15 Claims, 2 Drawing Sheets

DEW SENSOR HAVING A CONDUCTIVE POWER-CONTAINING MOISTURE SENSING MATERIAL DISPOSED BETWEEN OPPOSING ELECTRODES

BACKGROUND OF THE INVENTION

1. Technical Field

The present invention relates to a dew sensor used in a video tape recorder or other electronic appliance, and an electronic appliance using the same.

2. Related Art

In a video tape recorder, a dew sensor is used to stop rotation of a cylinder promptly if dew condensates on the cylinder mounting magnetic heads due to changes in the surrounding environment. The dew sensor is designed to detect dew condensation of the cylinder, and stop the rotation of the cylinder promptly, and keep the cylinder rotation stopped until dew condensation of the cylinder is eliminated. It is hence required to detect correctly the presence or absence of dew condensation on the surface of the rotating cylinder.

It was considered to mount the dew sensor directly on the cylinder, but mounting was difficult, assembling required much labor, and productivity was inferior.

Recently, as shown in FIG. 5, a dew sensor 24 was installed near the mounting area of a cylinder 23 of a chassis 22 adjacent to a cassette garage 21 of a video tape recorder main body 20. The dew sensor cannot be mounted on a printed circuit board 25 composing a specific circuit mounting various electronic components. The reason for this is that the material of the cylinder 23 is usually aluminum, and hence the thermal capacity is large. Therefore, when dew condenses, it takes a very long time until dew condensation is eliminated when left in a natural state. When the dew sensor 24 is mounted on the printed circuit board 25, since the printed circuit board 25 is higher in temperature than the cylinder 23, the surface of the dew sensor 24 dries earlier. As a result, although the state of dew condensation continues on the cylinder 23, a dew sensor on the printed circuit board 25 indicated that "dew condensation was eliminated." Owing to this reason, the dew sensor could not be mounted on the printed circuit board.

In such prior art, in order to eliminate detection error, the dew sensor 24 was disposed as closely to the cylinder 23 as possible. In this case, however, in order to dispose the dew sensor 24 near the cylinder 23 of the chassis 22, other wiring is needed, which was a bottleneck for productivity in assembling.

It was also attempted to adjust the reset time after dew condensation in order to install a timer for preventing detection error. Such timer only added an extra cost.

It is hence a primary object of the invention to eliminate the defects of the prior art by providing a dew sensor that can be mounted on a printed circuit board, which is capable of detecting correctly the dew condensation state of the cylinder.

SUMMARY OF THE INVENTION

A dew sensor of the present invention comprises a pair of opposing electrodes, and a moisture sensing material contacting and disposed between the pair of electrodes. The moisture sensing material is composed of a cured resin formed by reaction between a moisture absorbing resin possessing both a hydrophilic group and an epoxy group within a molecule, and a hardener containing a hydrazine derivative having a hydantoin skeleton. A conductive powder is also dispersed in the cured resin.

According to the present invention, a dew sensor excellent in sensitivity, quick in response, and small in detection errors of dew condensation is obtained. At the same time, a dew sensor capable of adjusting the reset characteristic can be obtained, and hence the location of the dew sensor is not limited. Thus, the dew sensor can be disposed at any desired position in the appliance, which increases the degree of freedom in design of the appliance. Moreover, by mounting the dew sensor, for example, on the printed circuit board, wiring of connection lead wires is substantially saved, and a low cost is realized.

In this composition, the dew sensor using a hardener containing a hydrazine derivative having a hydantoin skeleton and a long chain diamine compound is characterized by having extremely small detection errors of dew condensation, in addition to the above effects. As the long chain diamine, in particular, an aliphatic diamine compound is preferred.

REFERENCE NUMERALS

1 Insulated substrate
2, 3 Electrodes
4 Moisture sensing material
5, 6 Leads

DETAILED DESCRIPTION OF THE INVENTION

Figure 1:
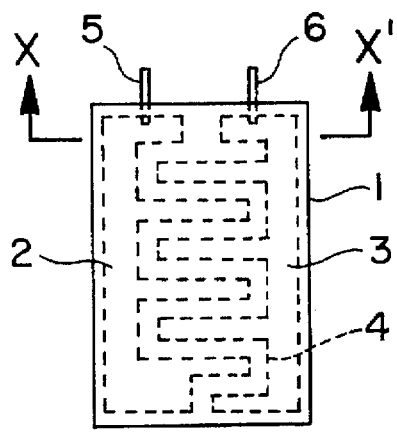
FIG. 1 is a plan view showing an embodiment of a dew sensor of the invention.
Figure 2:
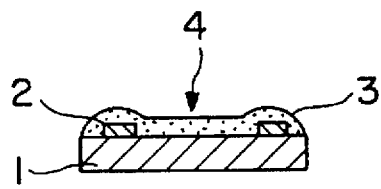
FIG. 2 is a sectional view along line X–X' in FIG. 1.

An embodiment of the invention is depicted in FIG. 1, which is a top view showing an embodiment of a dew sensor of the invention. FIG. 2 is its sectional view.

In FIG. 1 and FIG. 2, a pair of mutually interleaved electrodes 2 and 3 are mounted on an insulated substrate 1. In contact with the pair of electrodes 2, 3, a moisture sensing material 4 is disposed between the electrode 2 and electrode 3 so as to cover the electrodes. The moisture sensing material 4 is composed of a cured resin formed by a crosslinking reaction between a moisture absorbing resin possessing a hydrophilic group and an epoxy group in a molecule, and a hardener, with a conductive powder dispersed in the moisture absorbing resin. The hardener is composed of a hydrazine derivative having a hydantoin skeleton. In particular, a hardener containing a hydrazine derivative having a hydantoin skeleton and a long chain diamine compound is preferred. Leads 5, 6 are connected to the electrodes 2, 3.

In this composition, swelling and shrinking of the moisture sensing material due to humidity changes are detected as changes of contact resistance of the dispersed conductive powder. That is, when the ambient humidity of the dew sensor increases, the moisture sensing material absorbs the moisture, and swells. When the moisture sensing material is swollen, the conductive powder particles disposed in the moisture sensing material tend to separate from each other, and hence the electric resistance of the moisture sensing material increases. By contrast, when the ambient humidity of the dew sensor decreases, the moisture sensing material releases moisture and shrinks. When the moisture sensing material shrinks, the conductive powder disposed in the moisture sensing material tends to contact with each other, and hence the electric resistance of the moisture sensing material decreases.

Figure 3:
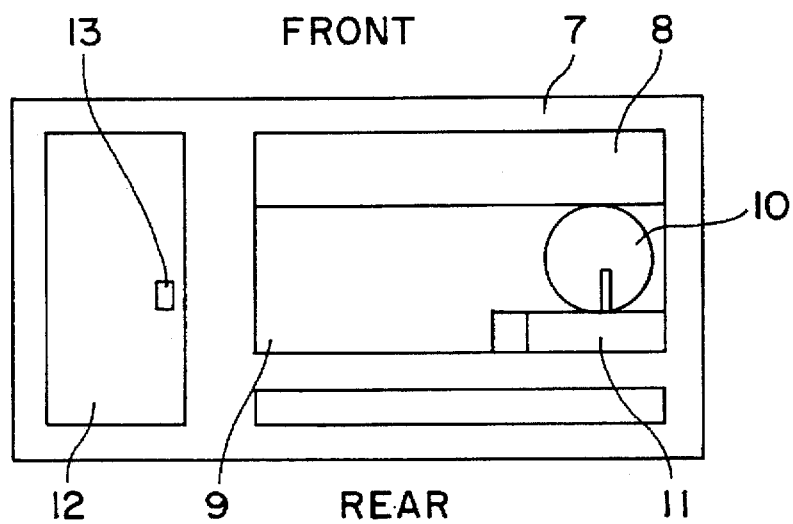
FIG. 3 is an explanatory diagram showing the state of mounting the dew sensor of the invention on a video tape recorder.

A video tape recorder mounting the dew sensor of such constitution is shown in FIG. 3. In FIG. 3, a cylinder 10 and a head amplifier 11 are mounted on a chassis 9 close to a cassette garage 8 of a video tape recorder main body 7. A dew sensor 13 is mounted on a printed circuit board 12 composing a desired circuit by incorporating various electronic components. In this way, the dew sensor 13 can be mounted on the independent printed circuit board 12, not adjacent to the cylinder 10 for driving the tape or the head amplifier 11.

The dew sensor of the invention is ideal as a sensor for detecting dew condensation on a rotary cylinder in video appliances which are advanced in the trend of smaller size and lighter weight. Using this dew sensor by mounting it on the printed circuit board, it is possible to design a desired moisture sensing characteristic, depending on the location of the printed circuit board. The dew sensor disposed at a desired position of the video appliance responds to dew condensation of the cylinder at high fidelity and at high sensitivity. Hence, it is also effective to help in reducing the size of the video appliance.

Figure 4:
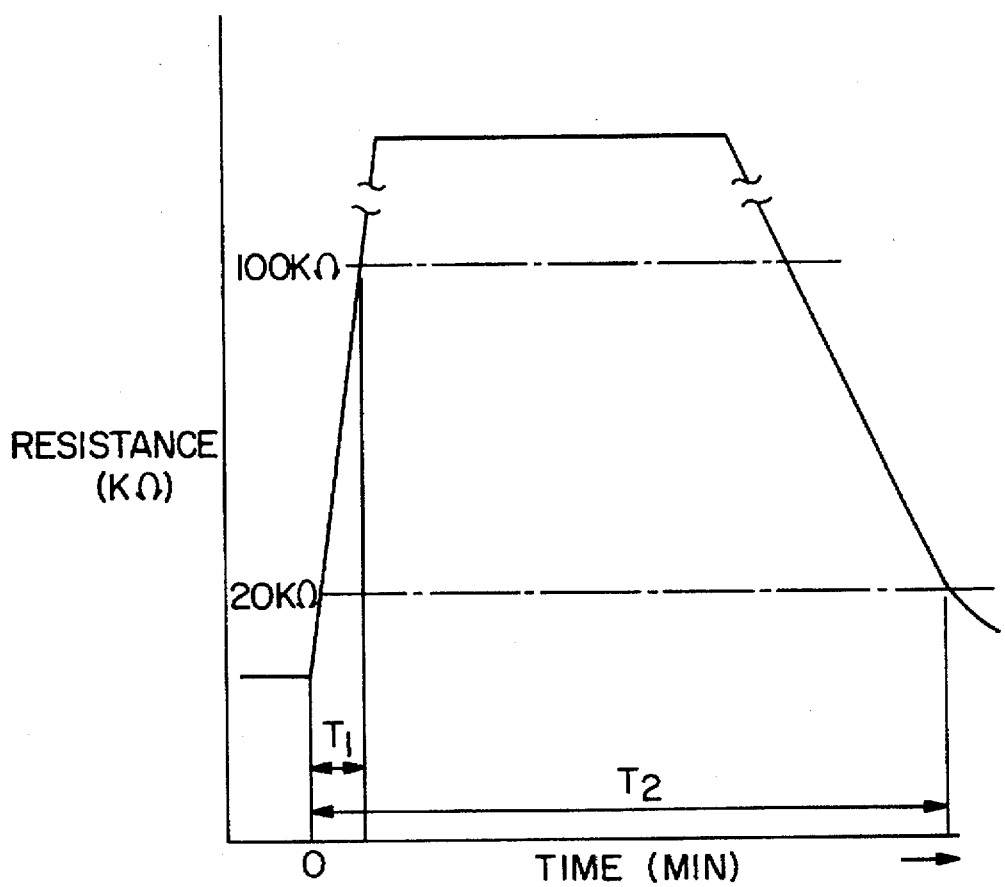
FIG. 4 is a characteristic diagram for explaining the dew condensation characteristic of the video tape recorder incorporating the dew sensor of the invention.
Figure 5:
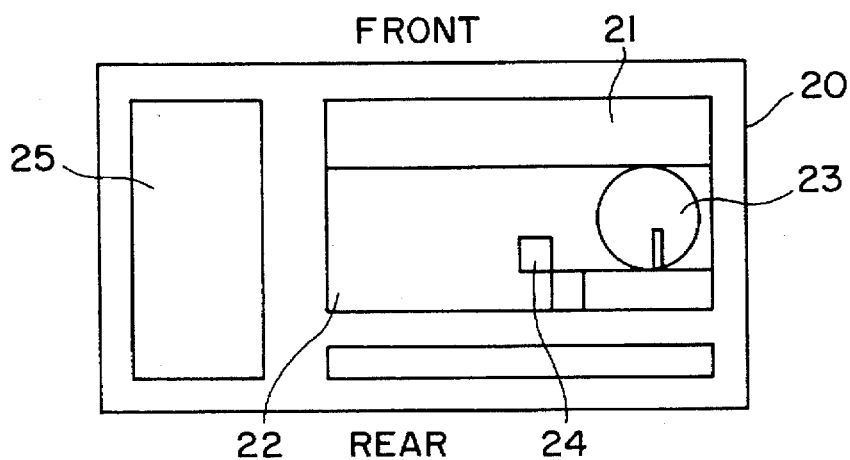
FIG. 5 is an explanatory diagram showing the mounting state of a video tape recorder incorporating a conventional dew sensor.

When dew sensor 13, first installed in the video appliance as shown in FIG. 3 and being held at 0° C., is taken out to an atmosphere of 25° C. and 75% RH, dew is condensed. The time required for spontaneous elimination of dew condensation and resistance value changes are shown in FIG. 4. The time from detection of dew condensation by the dew sensor 13 until the electric resistance value of the dew sensor reaches 100KΩ is defined to be $T_1$. The time from elimination of dew condensation on the dew sensor until the resistance value reaches 20KΩ is defined to be $T_2$. In the dew sensors of the embodiment described below, $T_1$ and $T_2$ were measured. On the other hand, the actual dew condensation elimination time on the cylinder 10 was 40 minutes. The difference between 40 minutes and $T_2$ was defined as dew condensation error. When this dew condensation error is close to 0, the dew sensor is evaluated to be high in reliability. In contrast, when the dew condensation error is large, the dew condensation state of the cylinder 10 is not detected accurately, and the dew sensor is not suited to mounting on the printed circuit board 12.

In the invention, the material of the insulated substrate 1 is not particularly limited, but a less moisture-absorbing material is selected, such as ceramics, glass, inorganic material, and plastics. As the pair of electrodes, although not particularly limited, ordinary coated element electrodes of conductive paint or carbon, and the like, may be used.

As the moisture absorbing resin, a resin having a hydrophilic group and an epoxy group is preferred. To control the moisture absorption or mechanical strength, a resin having a hydrophilic group, a hydrophobic group, and an epoxy group, may be also used. For example, a moisture absorbing material having a hydrophilic group and an epoxy group may be manufactured by a copolymerization reaction of vinyl monomer having a hydrophilic group and vinyl monomer having an epoxy group. A moisture absorbing resin having hydrophilic group, hydrophobic group and epoxy group may be manufactured by copolymerization reaction of vinyl monomer having a hydrophilic group, vinyl monomer having a hydrophobic group, and vinyl monomer having an epoxy group.

As the hardener, a hydrazine derivative having a hydantoin skeleton is used. It is particularly desired to use a hardener combining a hydrazine derivative having a hydantoin skeleton and a long chain diamine compound. The hydrazine derivative having a hydantoin skeleton acts to have a moisture retaining effect of the produced moisture sensing material. That is, water is easily coordinated (hydrated) with the carbonyl group of the hydantoin skeleton, and the moisture absorbing speed and swelling speed of the moisture sensing material are accelerated, and hence $T_1$ of the dew sensor becomes smaller. On the other hand, once coordinated (hydrated) with the carbonyl group of the hydantoin skeleton, water is hard to be dissociated, and the moisture releasing speed and shrinking speed of the moisture sensing material are decelerated, and hence $T_2$ of the dew sensor becomes larger. The long chain diamine compound provides the moisture sensing material with flexibility, and makes the moisture sensing material easier to swell and shrink, so that the sensitivity of the dew sensor may be enhanced. By curing through a crosslinking reaction of moisture absorbing resin and hardener, a moisture sensing material containing conductive powder is produced.

Since the functional group having moisture retaining effect and conductive powder are contained in the crosslinked cured resin, a highly functional sensor excellent in reproducibility is realized for the first time. The reason why the compound having such hydantoin skeleton possesses the moisture retaining effect is considered that hydration (or coordination of water) occurs easily in the diketone of the hydantoin skeleton. As the hydrazine group is crosslinked with epoxy resin, a moisture sensing material excellent in reproducibility is produced. Further, by combining with an aliphatic long chain diamine compound, flexibility is provided, the response and reset characteristics of the dew sensor are enhanced, and dew condensation errors are decreased significantly.

The moisture absorbing resin used in the invention is obtained by polymerizing the monomer having a hydrophilic group. Examples of monomer having hydrophilic group include moisture absorbing (meth)acrylate, moisture absorbing (meth)acrylamides, and vinyl pyrrolidone. Herein, (meth)acrylate is defined to mean acrylate or methacrylate. Similarly, (meth)acrylamide is defined to mean acrylamide or methacrylamide. The same definition is applied to the following specific compounds.

The moisture absorbing (meth)acrylate includes hydroxy lower alkyl (meth)acrylate and hydroxy lower alkoxy (meth) acrylate. Of these compounds, preferred vinyl monomers are 2-hydroxy ethyl (meth)acrylate, diethylene glycol mono (meth)acrylate, 2-hydroxy propyl(meth)acrylate, 3-hydroxy propyl(meth)acrylate, triethylene glycol mono(meth) acrylate, dipropylene glycol mono(meth)acrylate, etc. Examples of (meth)acrylamides include (meth)acrylamide, methylol (meth)acrylamide, and diacetone (meth) acrylamide, among others. Vinyl pyrrolidones include N-vinyl pyrrolidone, 2-methyl-N-vinyl pyrrolidone, etc. Vinyl monomers having an epoxy group include glycidyl (meth)acrylate, p-vinyl glycidyl benzoate, etc.

As the hydrophobic monomer, tetrahydrofurfuryl (meth) acrylate, 2-ethyl hexyl (meth)acrylate, lauryl (meth)acrylate, and others are preferred.

As the hydrazine derivative containing hydantoin skeleton, which is the hardener used in the invention, 1,3-bis(hydrazinocarboethyl)-5-isopropylhydantoin (abbreviated as hardener H hereinafter) and others may be preferred. The chemical formula of hardener H is as follows.

$$\begin{array}{c} (CH_3)_2CH \\ \diagdown \\ CH-C=O \\ \diagup \qquad \diagdown \\ H_2NHNCCH_2CH_2N \qquad NCH_2CH_2CNHNH_2 \\ \| \qquad \diagdown C \diagup \qquad \| \\ O \qquad \| \qquad O \\ \qquad O \end{array}$$

As the long chain diamine compound, flexible diamine compounds that can be crosslinked with epoxy resin can be used. For example, an aliphatic diamine compound having alkyl group with five or more carbon atoms and two amino groups may be preferred. As the aliphatic diamine compound, in particular, aliphatic 1,12-diaminododecane, 1,10-diaminodecane, 1,8-diaminooctane, and the like, may be preferred. A combination of aliphatic diamine compound and aromatic diamine compound may be also used, and it is possible to adjust the response or reset characteristic by varying the flexibility of the moisture sensing material to be produced. As the aromatic diamine compound, for example, 4,4'-diaminodiphenyl methane, and the like, may be used.

As the conductive powder, acetylene black, carbon black, graphite, metal powder, silver powder, copper, other metal powder, or a mixture thereof, may be used. The content of the conductive powder is preferred to be about 15 to 40 parts by weight of 100 parts by weight of the moisture absorbing resin. More preferably, the conductive powder should be present in about 20 to 30 parts by weight. When the content of the conductive powder is less than about 15 parts by weight, the resistance value of the moisture sensing material is too high, and sufficient reproducibility is hardly obtained. By contrast, if the content of the conductive powder is more than about 41 parts by weight, the resistance value of the moisture sensing material is too low, and the response of resistance change depending on temperature change drops.

An example of a manufacturing method for the dew sensor of the present invention is described below. First, the moisture absorbing resin and hardener are dissolved in a solvent. Conductive powder is added to the solvent, and a mixed solution sufficiently dispersing the conductive powder is obtained. Afterwards, to cover a pair of comb-shaped electrodes 2, 3 provided on an insulated substrate 1, the mixed solution is laminated between the electrode 2 and electrode 3. By heating the laminated mixed solution, the solvent is evaporated away, and the moisture absorbing resin and hardener are crosslinked. In this way, the moisture sensing film (that is, the moisture sensing material) containing a dispersed conductive powder is disposed between the electrode 2 and electrode 3 so as to cover the pair of electrodes 2, 3. As the pair of electrodes 2, 3, conductive paint and ordinary electrode material can be used.

The resistance value of the dew sensor can be freely set by selecting the amount of the conductive powder dispersed in the resin.

Further specific embodiments of the invention are described below.

(Embodiment 1)

In 110 g of ethyl cellosolve, 19.5 g of 2-hydroxy ethyl methacrylate, 1.42 g of glycidyl methacrylate, and 19 mg of azobisisobutyronitrile as polymerization initiator were dissolved. The solution was heated for 5 hours at 80° C. in a nitrogen stream to copolymerize. After reaction, by pouring the solution into ether, the produced polymer was sedimented and separated. The produced polymer was refined in methanol-ether system, and was further dried in vacuo at room temperature, and a moisture absorbing resin was obtained. In 20 g of ethyl cellosolve, 2 g of this moisture absorbing resin is dissolved, and 0.5 g of acetylene black with mean particle size of 40 μm is added as conductive powder together with 7 g of benzyl alcohol, and their mixture is sufficiently kneaded by three rolls. Next, as hardener, 19.8 mg of 1,3-bis(hydrazinocarboethyl)-5-isopropylhydantoin(hardener H) and 37.8 mg of 1,12-diaminodecane are dissolved in a small amount of benzyl alcohol. By adding the solution to the mixture, a paste mixture is obtained.

On the ceramic insulated substrate 1 as shown in FIG. 1, a pair of comb-shaped carbon electrodes 2, 3 are formed. To cover the carbon electrodes 2 and 3, the paste mixture is applied between the electrode 2 and electrode 3. By heating the applied paste mixture for 30 minutes at 150° C., a solid coat film of cured moisture sensing material is formed. Thus, the dew sensor is manufactured.

(Comparison 1)

A dew sensor was fabricated by the same method as in embodiment 1, except that 50 mg of 4,4'-diaminophenylmethane was used as hardener.

(Comparison 2)

A dew sensor was fabricated by the same method as in embodiment 1, except that 50.4 mg of 1,12-diaminododecane was used as hardener.

(Embodiment 2)

As the material of the moisture absorbing resin of embodiment 1, further 7.8 g of tetrahydrofurfuryl methacrylate as hydrophobic monomer was added to copolymerize the composition, and a moisture absorbing resin was synthesized. To 2 g of this moisture absorbing resin, 13.9 mg of hardener H and 22.8 mg of 1,10-diaminodecane were added, and a dew sensor was fabricated in the same manner as in embodiment 1.

(Comparison 3)

A dew sensor was fabricated by the same method as in embodiment 2, except that 35 mg of 4,4'-diaminophenylmethane was used as hardener.

(Comparison 4)

A dew sensor was fabricated by the same method as in embodiment 2, except that 35.3 mg of 1,12-diaminododecane was used as hardener.

(Embodiment 3)

A moisture absorbing resin was synthesized by copolymerizing a composition of acrylamide:2-ethylhexyl methacrylate: p-vinyl glycidyl benzoate at a ratio of 10:9:1 by weight. To 2 g of this moisture absorbing resin, 30 mg of hardener H and 49.4 mg of 1,10-diaminodecane were added, and a dew sensor was fabricated in the same method as in embodiment 1.

(Comparison 5)

A dew sensor was fabricated by the same method as in embodiment 3, except that 76 mg of 4,4'-diaminophenylmethane was used as hardener.

(Comparison 6)

A dew sensor was fabricated by the same method as in embodiment 3, except that 76.7 mg of 1,12-diaminododecane was used as hardener.

(Embodiment 4)

A dew sensor was fabricated by the same method as in embodiment 3, except that 30 mg of hardener H, 33 mg of 1,10-diaminodecane, and 19 mg of 4,4-diaminodiphenylmethane were used as hardener.

(Embodiment 5)

A dew sensor was fabricated by the same method as in embodiment 1, except that only 1,3-bis(hydrazinocarboethyl)-5-isopropylhydantoin (hardener H) was used as hardener.

For these fabricated dew sensors, $T_1$ and $T_2$ were measured, and the results are shown in Table 1, together with the dew condensation error $(40-T_2)$.

TABLE 1

|  | $T_1$ (min) | $T_2$ (min) | Dew condensation error $40 - T_2$ (min) |
| --- | --- | --- | --- |
| Embodiment 1 | 2.0 | 42 | −2 |
| Comparison 1 | 4.0 | 20 | 20 |
| Comparison 2 | 3.5 | 18 | 22 |
| Embodiment 2 | 1.9 | 41 | −1 |
| Comparison 3 | 3.8 | 18 | 22 |
| Comparison 4 | 3.4 | 17 | 23 |
| Embodiment 3 | 2.5 | 44 | −4 |
| Comparison 5 | 4.5 | 19 | 21 |
| Comparison 6 | 4.2 | 18 | 22 |
| Embodiment 4 | 2.6 | 41 | −1 |
| Embodiment 5 | 2.0 | 50 | −10 |

As shown in Table 1, the dew sensor using a moisture sensing material produced from a moisture absorbing resin obtained by copolymerization of monomer having hydrophilic group and monomer having glycidyl group, and a hardener composed of hydrazine derivative having a hydantoin skeleton and long chain diamine, such as the dew sensor in embodiment 1, is small in $T_1$ (superior in sensitivity), and small in dew condensation errors. By contrast, as in comparisons 2 and 3, the dew sensor using the hardener not containing a hydrazine derivative having a hydantoin skeleton is large in $T_1$ (inferior in sensitivity), and large in dew condensation errors.

The dew sensor using a moisture sensing material produced from a moisture absorbing resin obtained by copolymerization of monomer having hydrophilic group, monomer having hydrophobic group, and monomer having glycidyl group, and a hardener composed of hydrazine derivative having hydantoin skeleton and long chain diamine, such as the dew sensor in embodiment 2, is small in $T_1$ (superior in sensitivity), and small in dew condensation errors. By contrast, as in comparisons 3 and 4, the dew sensor using the hardener not containing hydrazine derivative having a hydantoin skeleton is large in $T_1$ (inferior in sensitivity), and large in dew condensation errors.

The dew sensor using a moisture sensing material produced from a moisture absorbing resin obtained by copolymerization of monomers having two types of hydrophilic groups and monomer having glycidyl group, and a hardener composed of hydrazine derivative having a hydantoin skeleton and long chain diamine, such as the dew sensor in embodiment 3, is small in $T_1$, and small in dew condensation errors. By contrast, as in comparisons 5 and 6, the dew sensor using the hardener not containing a hydrazine derivative having a hydantoin skeleton is large in $T_1$ (inferior in sensitivity), and large in dew condensation errors.

The dew sensor using a moisture sensing material produced from a moisture absorbing resin obtained by copolymerization of monomers having two types of hydrophilic groups and monomer having glycidyl group, and a hardener composed of a hydrazine derivative having a hydantoin skeleton, long chain diamine and aromatic diamine compound, such as the dew sensor in embodiment 4, is small in $T_1$, and small in dew condensation errors.

The dew sensor using a moisture sensing material produced from a moisture absorbing resin obtained by copolymerization of monomer having hydrophilic group and monomer having glycidyl group, and a hardener composed only of a hydrazine derivative having a hydantoin skeleton, such as the dew sensor in embodiment 5, is small in $T_1$ (superior in sensitivity), and small in dew condensation errors. That is, water is easy to be coordinated (hydrated) with the C=O group of the hydantoin skeleton, and the moisture absorbing speed is accelerated, so that $T_1$ becomes smaller. However, once coordinated (hydrated) in the hydantoin skeleton, water is hard to dissociate, and the shrinking speed of the moisture sensing material is slow, and hence $T_2$ is larger than in embodiment 1.

Thus, comparing the embodiments and comparative examples, in the embodiments (embodiments 1, 2, 3, 4, 5) composing the moisture sensing material produced from the moisture absorbing resin having a hydrophilic group and an epoxy group and a hydrazine derivative having a hydantoin skeleton, $T_1$, is small, that is, sensitivity is superior, and the dew condensation errors are small. It is thus known that the dew sensors of embodiments 1, 2, 3, 4, 5 are suited as dew sensors when mounted on the printed circuit board.

By contrast, in the comparative examples (comparisons 1, 2, 3, 4, 5, 6) not containing the hardener H, $T_1$ is large and hence the sensitivity is inferior. Moreover, in the dew sensors of the comparative examples, $T_2$ is considerably smaller than 40 minutes, and dew condensation errors are large. Hence, although dew condensation is not actually eliminated in the cylinder, it is judged that dew condensation is eliminated. It is therefore evident that the dew sensors of the comparative examples are not suited as sensors to be mounted on the printed circuit board.

As described herein, a dew sensor using a moisture sensing material composed of a moisture absorbing resin having an epoxy group in its molecule, a crosslinked cured material produced by reaction with a hardener containing a hydrazine derivative having a hydantoin skeleton, and conductive material dispersed in the cured material is high in sensitivity, quick in response, and small in dew condensation errors. Moreover, at the same time, the dew sensor capable of adjusting the reset characteristic can be obtained, and hence the location of the dew sensor is not limited, so that the dew sensor can be installed in any desired position in the appliance. As a result, the degree of freedom in design of the appliance is increased. Furthermore, for example, by mounting the dew sensor on the printed circuit board, wiring work of connection lead wires may be substantially saved, and a lower cost may be realized.

In this construction, the dew condensation sensor using the hardener containing hydrazine derivative having a hydantoin skeleton and long chain diamine compound is, in addition to the above effects, characterized by the effect of extreme reduction of dew condensation errors.

What is claimed is:

1. A dew sensor comprising:
    a pair of opposing electrodes;
    a moisture sensing material contacting and disposed between said pair of electrodes; and
    a conductive powder dispersed in the moisture sensing material,
    wherein the moisture sensing material is composed of a cured resin produced by reaction between a moisture absorbing resin having a hydrophilic group and an epoxy group, and a hardener containing a hydrazine derivative having a hydantoin skeleton.

2. The dew sensor of claim 1, wherein the hardener contains the hydrazine derivative having a hydantoin skeleton and a long chain diamine compound.

3. The dew sensor of claim 2, wherein the long chain diamine compound is an aliphatic diamine compound.

4. The dew sensor of claim 1, wherein the hardener contains the hydrazine derivative having a hydantoin skeleton, an aliphatic diamine compound, and an aromatic diamine compound.

5. The dew sensor of claim 1, wherein the hydrazine derivative having a hydantoin skeleton is 1,3-bis (hydrazinocarboethyl)-5-isopropylhydantoin.

6. The dew sensor of claim 1, wherein the moisture absorbing resin is produced by the copolymerization reaction of a monomer having at least one hydrophilic group, and a monomer having a glycidyl group.

7. The dew sensor of claim 6, wherein the hydrophilic group is a hydroxy group or an amide group.

8. The dew sensor of claim 1, wherein the moisture absorbing resin is produced by the copolymerization reaction of a monomer having a hydrophilic group, a monomer having a hydrophobic group, and a monomer having a glycidyl group.

9. The dew sensor of claim 1, wherein the content of the conductive powder is in a range of about 15 parts to about 40 parts by weight of 100 parts by weight of the moisture absorbing resin.

10. A dew sensor comprising:

an electrically insulated substrate;

a pair of opposing electrodes mounted on the insulated substrate; and a moisture sensing material contacting and disposed between said pair of electrodes; and conductive powder dispersed in the moisture sensing material, wherein the moisture sensing material is composed of a cured resin produced by reaction between a moisture absorbing resin having a hydrophilic group and an epoxy group, and a hardener containing a hydrazine derivative having a hydantoin skeleton.

11. The dew sensor of claim 10, wherein the hardener contains the hydrazine derivative having a hydantoin skeleton and an aliphatic diamine compound.

12. The dew sensor of claim 10, wherein each one of said electrodes has a comb shape.

13. An electronic appliance having a printed wiring board on which the dew sensor of claim 10 is mounted.

14. The electronic appliance of claim 13, wherein the electronic appliance is a video tape recorder.

15. The electronic appliance of claim 14, wherein the dew sensor is disposed at a position remote from a cylinder installed in the video tape recorder, and the dew sensor detects a state of dew condensation on the cylinder.

* * * * *